United States Patent [19]

Green

[11] Patent Number: 4,700,005
[45] Date of Patent: Oct. 13, 1987

[54] PREPARATION OF PHENOLIC ETHERS

[75] Inventor: Michael J. Green, Yateley, Nr. Camberley, England

[73] Assignee: BP Chemicals Limited, London, England

[21] Appl. No.: 871,504

[22] Filed: Jun. 6, 1986

[30] Foreign Application Priority Data

Jun. 14, 1985 [GB] United Kingdom ............... 8515179

[51] Int. Cl.$^4$ ..................... C07C 149/32; C07C 41/00
[52] U.S. Cl. ...................................... 568/38; 568/630; 568/632; 568/648; 568/658
[58] Field of Search ............... 568/632, 630, 648, 658, 568/38

[56] References Cited

U.S. PATENT DOCUMENTS 4,192,949 3/1980 Merger et al. .................. 568/630 X Primary Examiner—Howard T. Mars
Attorney, Agent, or Firm—Brooks Haidt Haffner & Delahunty

[57] ABSTRACT

Phenolic ethers are produced by reacting a phenol with a compound selected from an alkyl halide, an aryl halide, a dialkyl sulphate and a diaryl sulphate in the presence as catalyst of an amidine.

20 Claims, No Drawings

PREPARATION OF PHENOLIC ETHERS

The present invention relates to the production of phenolic ethers. More particularly, the present invention relates to the production of phenolic ethers by the base promoted reaction of phenols with a compound selected from an alkyl halide, an aryl halide, a dialkyl sulphate or a diaryl sulphate.

It is known that phenolic ethers can be prepared by the reaction of phenols, alkyl halides and sodium alkoxide reagents. These sodium alkoxides however have a number of disadvantages which can cause problems when the reaction is conducted on a commercial scale. For example, the alkoxide salts pose considerable health and safety problems and are sensitive to oxygen. Thus, the storage and use of alkoxide salts on a commercial scale requires special apparatus.

A second disadvantage of the sodium alkoxide catalyst is that it cannot be regenerated after the reaction has occurred. With conventional sodium alkoxides, the metal is lost from the system as a sodium halide. Furthermore, precipitation "in situ" can cause fouling of equipment.

It has now been discovered that Lewis bases such as amidines can be used to promote the formation of phenolic ethers from the reaction of phenols with alkyl halides, aryl halides, dialkyl sulphates or diaryl sulphates. Such bases are oxygen stable and regenerable, thereby avoiding many of the problems associated with the use of sodium alkoxides.

Accordingly, the present invention provides a process for the production of phenolic ethers which process comprises reacting a phenol with a compound selected from an alkyl halide, an aryl halide, a dialkyl sulphate and a diaryl sulphate in the presence as catalyst of an amidine.

The phenol reactant used in the process of the present invention can be phenol itself; straight-chain or branched-chain acyclic hydrocarbyl substituted phenols such as $C_1$ to $C_{12}$ alkyl phenols or $C_2$ to $C_{12}$ alkenyl phenols; thiophenols (benzenethiols) and polyhydroxybenzenes. Examples of suitable phenols include but are not limited to phenol, methylphenol, butylphenol, ethenylphenol, 1,2-dihydroxybenzene, 1,4-dihydroxybenzene (hydroquinone), 1,3,5-trihydroxybenzene, benzenethiol, 1,2-benzenedithiol. Preferred phenol reactants are $C_1$ to $C_{12}$ alkyl phenols and most preferred are $C_1$ to $C_4$ alkyl phenols.

Suitable alkyl halides include $C_1$ to $C_{12}$ alkyl chlorides, bromides and iodides. Examples of suitable aryl halides include phenyl chlorides, bromides or iodides and naphthyl chlorides, bromides or iodides. The dialkyl sulphates are preferably sulphates containing two $C_1$ to $C_{20}$ alkyl substituents, such as dimethyl or diethyl sulphate. The diaryl sulphates are sulphates containing two aryl substituents, such as diphenyl sulphate. Examples of aryl substituents include but are not limited to phenyl, naphthyl and alkyl substituted phenyls and naphthyls. Although any of the above reactants can be employed in the process of the present invention, straight-chain alkyl chlorides, bromides or iodides are preferred and most preferred are $C_1$ to $C_{10}$ straight-chain alkyl chlorides, bromides and iodides.

By the term amidine is meant a compound containing the grouping:

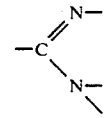

Conveniently the free valencies on the nitrogen atom are attached to carbon atoms or hydrogen atoms and the free valency on the carbon is attached to either carbon or nitrogen atoms. In the last mentioned case where the carbon atom is attached to a nitrogen atom, the structure will comprise a guanidine grouping and the compound containing this grouping is a guanidine.

A preferred class of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine, then any two of the three nitrogen atoms may be in the same or different rings. Those nitrogen atoms which are not part of any rings may form part of a substituted or unsubstituted hydrocarbyl group.

A preferred class of cyclic amidines is that in which the amidine group can form part of a fused ring system containing 6- and 5-membered rings or 6- and 7-membered rings or two six-membered rings, as for example in 1,5-diazabicyclo[4.3.0.]non-5-ene (DBN), 1,8-diazabicyclo[5.4.0.]undec-7-ene (DBU) or 1,5,7-triazabicyclo[4.4.0.]dec-5-ene (TBD).

The amidine may be added to the reaction mixture either on its own or as a solution in a suitable alcohol solvent and is suitably added in stoichiometric amounts corresponding to the concentration of the phenol reactant.

The amidine can be supported, that is chemically and physically bonded, to an inert solid and then added to the reaction mixture. In the supported form of the catalyst the surface atoms of the solid are bonded to one or more of the free valencies of the amidine or guanidine group either directly or through an intermediate hydrocarbyl radical. In the case of cyclic amidines or guanidines the hydrocarbyl radical may constitute part of the ring structure of the molecule. The amidine is bonded to the support by conventional techniques known to those skilled in the art.

The inert solid may be either organic, for example a polymer, copolymer, resin and the like or it may be inorganic such as a silica, aluminosilicate, alumina, diatomaceous earth, zeolite, clay, and the like.

It is preferred to carry out the reaction at elevated temperature. The preferred range of reaction temperatures will vary depending on the exact reactants used but the temperature is typically in the range of from 50° to 150° C.

With regard to the pressure, the reaction may be conducted at atmospheric pressure or, in the case where the reaction is conducted in a closed vessel, under the autogenous pressure of the reactants at the reaction temperature. Elevated pressures can be employed if desired.

It is also preferred to conduct the reaction in the liquid phase in a suitable solvent. Preferred solvents are alcohols, particularly lower alcohols such as methanol and ethanol. The process may be operated in either a continuous or batch mode.

The present invention is illustrated by the following Examples. However, these Examples should not be construed as limiting the scope of this invention which includes equivalent modifications, variations and embodiments.

EXAMPLE 1

A 50 ml round-bottom flask fitted with a water cooled condenser was charged with 30 ml of ethanol, 4.7 g of phenol, 7.6 g of 1,8-diazabicyclo[5.4.0]undec-7-ene (DBU) and 8.5 g of 1-iodopropane. The contents of the flask were refluxed for 3 hours. Analysis of the cooled liquid product by gas chromatography showed a 76% conversion of phenol to n-propyl phenyl ether.

EXAMPLE 2

A 50 ml round-bottom flask fitted with a water cooled condenser was charged with 15 g of methanol, 1.6 g of p-t-butylphenol, 7.5 g of DBU, and 1.7 g of n-propyl iodide and mixture refluxed for 3 hours. Analysis of the liquid product showed a 55% conversion of t-butylphenol to n-propyl t-butylphenyl ether.

EXAMPLE 3

Example 2 was repeated except that the flask was charged with 25 g of ethanol, 1.4 g of hydroquinone and 1.7 g of iodopropane. Analysis of the liquid product showed a 35% selectivity to 1,4-dipropoxybenzene and a 65% selectivity to 4-propoxyphenol.

EXAMPLE 4

Example 2 was repeated except that 1.1 g of thiophenol was used in place of p-t-butylphenol. Analysis of the liquid product showed a quantitative conversion of thiophenol to n-propyl phenyl thioether.

EXAMPLE 5

Example 2 was repeated except that 0.94 g of phenol was used in place of p-t-butylphenol and 1.8 g of 1-bromoheptane was used in place of n-propyl iodide. Analysis of the liquid product showed a 74.5% conversion of phenol to n-heptyl phenol to n-heptyl phenyl ether.

EXAMPLE 6

Example 2 was repeated except that 1.24 g of 1,5-diazobicyclo[4.3.0]non-5-ene (DBN) was used in place of DBU and 0.94 g of phenol was used in place of p-t-butylphenol. Analysis of the liquid product showed a 46% conversion of phenol to n-propyl phenyl ether.

EXAMPLE 7

Example 6 was repeated except that 1.39 g of 1,5,7-triazabicyclo[4.4.0]dec-5-ene (TBD) was used in place of DBU. Analysis of the liquid product showed a 77% conversion of phenol to n-propyl phenyl ether.

EXAMPLE 8

A 50 ml round-bottom flask was charged with 20 g of ethanol, 0.94 g of phenol, 1.5 g of 1,8-diazabicyclo[5.4.0]undec-7-ene (DBU) and 1.24 g of dimethyl sulphate. The contents of the flask were refluxed for 3 hours. Analysis of the cooled liquid product by gas chromatography showed a 67% conversion of phenol, with a total selectivity to anisole.

EXAMPLE 9

Example 8 was repeated except that 1.1 g of thiophenol was used in place of phenol. Analysis of the liquid product showed a 76.5% conversion of thiophenol, with a total selectivity to thioanisole.

I claim:

1. A process for the production of phenolic ethers which process comprises reacting a phenol with a compound selected from an alkyl halide, an aryl halide, a dialkyl sulphate and a diaryl sulphate in the presence as catalyst of an amidine.

2. A process according to claim 1 wherein the phenol is ether phenol itself, a straight-chain or branched-chain acyclic hydrocarbyl substituted phenol, a thiophenol or a polyhydroxybenzene.

3. A process according to claim 1 wherein the phenol is either a $C_1$ to $C_8$ alkyl phenol or a $C_2$ to $C_8$ alkenyl phenol.

4. A process according to claim 1 wherein the compound reacted with the phenol is a $C_1$ to $C_{12}$ alkyl chloride, bromide or iodide.

5. A process according to claim 4 wherein the alkyl halide is a $C_1$ to $C_{10}$ straight-chain alkyl chloride, bromide or iodide.

6. A process according to claim 1 wherein the compound reacted with the phenol is either a phenyl or a naphthyl chloride, bromide or iodide.

7. A process according to claim 1 wherein the compound reacted with the phenol is a sulphate containing two $C_1$ to $C_{20}$ alkyl substituents.

8. A process according to claim 1 wherein the compound reacted with the phenol is a sulphate containing two aryl substituents selected from phenyl, naphthyl, alkyl-substituted phenyl and alkyl substituted naphthyl substituents.

9. A process according to claim 1 wherein the amidine is a cyclic amidine.

10. A process according to claim 1 wherein the amidine is a guanidine.

11. A process according to claim 1 wherein the amidine is either 1,5-diazabicyclo[4.3.0]non-5-ene; 1,8-diazabicyclo[5.4.0]undec-7-ene or 1,5,7-triazabicyclo[4.4.0]dec-5-ene.

12. A process according to claim 1 wherein the amidine is supported.

13. A process according to claim 1 wherein the reaction is carried out in the liquid phase in the presence of a solvent which is an alcohol.

14. A process according to claim 1 wherein the reaction is carried out at an elevated temperature in the range from 50° to 150° C.

15. A process for the production of phenolic ethers which process comprises reacting a phenol selected from the group consisting of phenol itself, a straight-chain or branched-chain acyclic hydrocarbyl substituted phenol, a thiophenol and a polyhydroxybenzene, with a compound selected from the group consisting of an alkyl halide, an aryl halide, a dialkyl sulphate and a diaryl sulphate, at elevated temperature and in the presence as catalyst of a cyclic amidine.

16. A process according to claim 15, wherein the cyclic amidine is one in which the amidine group can form part of a fused ring system containing 6- and 5-membered rings or 6- and 7-membered rings or two six-membered rings.

17. A process according to claim 15, wherein the phenol is selected from the group consisting of phenol, p-t-butylphenol, hydroquinone and thiophenol.

18. A process according to claim 15, wherein said elevated temperature is in the range of 50° to 150° C.

19. A process according to claim 15, wherein the compound is an alkyl halide or a dialkyl sulphate.

20. A process accoridng to claim 19, wherein the compound is selected from the group consisting of 1-iodopropane, n-propyl iodide, 1-bromoheptane and dimethyl sulphate.

* * * * *